United States Patent [19]

Hager

[11] 4,001,400
[45] Jan. 4, 1977

[54] PRESERVATIVE FOR WOOD

[75] Inventor: Bror Olof Hager, Djursholm, Sweden

[73] Assignee: Hager Aktiebolag, Stockholm, Sweden

[22] Filed: Jan. 17, 1972

[21] Appl. No.: 218,546

[30] Foreign Application Priority Data

Jan. 26, 1971 Sweden ............... 880/71

[52] U.S. Cl. ............... 424/134; 424/141; 424/166; 424/294; 424/318; 21/7
[51] Int. Cl.$^2$ ............... A01N 13/00
[58] Field of Search ......... 424/294, 166, 157, 134, 424/141

[56] References Cited

UNITED STATES PATENTS

| | | | |
|---|---|---|---|
| 1,969,213 | 8/1934 | Eyre et al. | 424/294 X |
| 2,104,584 | 1/1938 | Dearborn | 424/294 X |
| 2,149,284 | 3/1939 | Gordon | 21/26 |
| 2,772,263 | 11/1956 | Yeager | 424/294 X |
| 3,018,196 | 1/1962 | Wagner | 424/294 X |
| 3,061,508 | 10/1962 | Morriss et al. | 424/294 X |
| 3,089,810 | 5/1963 | Hager | 424/141 X |
| 3,111,456 | 11/1963 | Hochman et al. | 424/294 |
| 3,323,987 | 6/1967 | Frensch | 424/294 |
| 3,474,172 | 10/1969 | Hill et al. | 424/294 |

OTHER PUBLICATIONS

Chemical Abstracts, vol. 51: 6926b (1957).
Chemical Abstracts, vol. 57: 5117g (1962).

*Primary Examiner*—Leonard Schenkman
*Attorney, Agent, or Firm*—Pierce, Scheffler & Parker

[57] ABSTRACT

The wood preservative of the present invention comprises an aqueous ammoniacal solution of a fatty acid salt of at least one metal of the group consisting of Cu, Zn, Ni, Cd and Co. The fatty acid contains 6–12 carbon atoms per molecule, and preferably caprylic acid.

10 Claims, No Drawings

PRESERVATIVE FOR WOOD

The present invention relates to preservatives for wood and other fibrous organic materials or products such as textiles, ropes, leather, paper, and wood pulp. The preservatives are mainly intended to protect against deterioration by decay and insects.

It is known that preservatives based on copper compounds can give wood and other fibrous materials a very good preservation. Against a few more rarely occurring destroying organisms the copper radical does not, however, have a higher effect. It is, therefore, an obvious advantage if in preservatives based on copper compounds there can also be introduced preserving agents which supplement or complete the preserving effect of the copper radical.

The preservatives are used in solution. After the treatment the agents are precipitated in the wood or other fibrous material to be treated in resistant form, in order to provide a permanent preservation. They must be resistant to leaching. They also must not evaporate, or be converted in situ to less effective compounds or compounds which can be leached out or be evaporated.

Preservatives intended to be used in aqueous solutions have mainly been prepared according to one or another of two different ways. According to the first way, the preservatives have been dissolved with the help of chromic acid, such for instance as preservatives according to U.S. Pat. No. 2,432,007. After introducing the solution into the material the chromic acid content is reduced — the chromium ion is converted from six valent acid radical to three valent positive radical - and as a result of this reduction the copper (metal) compounds are precipitated in the material. Preservatives of this kind have certain disadvantages, due to the highly acidic and oxidating character of the chromic acid. They are hazardous to handle, and they have also other hygienic inconveniences. The extreme chemical properties of the chromic acid limit the possibilities to select and to introduce different protecting agents in the preservative. The strong oxidating character means, further, that it will under conversion very quickly attack the wood and different substances in it. Therefore the preservative treatment has to be carried out rapidly otherwise the preservative will be converted too early — during the penetration of the solution — with an ensuing poor distribution in the wood as a consequence. All methods that need some time for being carried out — and some of them are important — can thus not be utilized. Furthermore, there is a risk that the chromic acid will attack the wood so severe that it loses a part of its strength.

According to the second way of preparing the preservatives, the same have been dissolved with the help of ammonia. This way has been considerably developed, - it is, for instance, described in U.S. Pat. Nos. 2,908,607 and 3,089,810. This mode of preparation gives many possibilities as regards varying the composition and the properties of the preservatives to make them adaptable for different purposes and methods of application. These preservatives can for instance be introduced into the wood by the Lowry or Ruping methods. These methods (see U.S. Pat. No. 3,560,251, column 1, lines 47–59 inclusive) do not fill the wood cells completely with preservative solution — they are "empty cell" methods — which is a definite advantage for the following drying of the wood. This is of a very special importance for methods of preservation, drying, and coloring according to U.S. Pat. No. 3,560,251. Some other methods for the application of these preservatives are discussed below.

As an active preserving agent supplementary to copper according to the above-mentioned U.S. Pat. No. 2,908,607 polychlorophenols have been used. In U.S. Pat. No. 3,089,810 arsenic and fluorine have also been proposed as supplements. At that time the use of chlorophenols was considered as a step forward in view of the preservative effect produced as well as of the hygienic properties. The greatly increased demands of hygiene have, however, lately caused a more strict attitude against chlorinated (also nitrated, etc.) products. It has therefore been looked upon as being an advantage if the chlorophenols could be replaced. Further the chlorophenols have a limited solubility in the preserving solutions. It has been necessary to prepare the solutions in a special way from two components. A precipitation risk has always been present.

The present invention develops the ammoniacal copper-containing preservatives by the use of some fatty acids as supplementing or completing agent to the copper radical. These acids have a high, and all-round, preserving effect with respect to wood-destroying fungi, to mould and to blue stain. Therefore they complete to a very high degree the effect of the copper radical. The fatty acids in question have also other desirable properties which are discussed below.

The preserving effect of the fatty acids increases more and more with a higher number of carbon atoms up to the acid with 11 carbon atoms. The effect reach a very high level. The acids with 8, 9, 10 and 11 carbon atoms can thus according to agar-tests kill the aggressive wood-destroying fungi *Fomus annosus* in amounts around one hundred of one per cent. Thereafter the "picture" changes. The acid with 12 carbon atoms has a still very high, but lower, effect. The acids with more carbon than 12 carbon atoms have a low (or no) effect.

As the lowest molecular weight fatty acids in the series do not have the same high effect as the higher ones they are not so suitable for use. Furthermore, the first acids do not form as difficultly soluble compounds with copper. Thus, they cannot be precipitated in the wood or other fibrous material to give a desirably permanent protection. These acids are, further, not so resistant to evaporation as are the higher ones and to some extent they may evaporate even if they are combined with copper.

The higher acids have, in addition to their high effect, other very good properties as wood preservatives. They are difficultly soluble in water; they have high boiling points. In spite of this they may not be looked upon as ideal wood preservatives to be used solely for outdoor use. The claims on resistance against leaching and evaporation are in practice so very high. It is when the acids are combined with copper to the production of extremely difficultly soluble and extremely difficultly volatile salts that they completely can fill their task for present purposes.

The fatty acids with many carbon atoms and a low (or no) effect cannot be dissolved by ammonia or in an ammoniacal copper solution. If more advanced steps are taken for the dissolution, the solvents employed will be too viscose for ordinary wood impregnation. The fatty acids with 11 and 12 carbon atoms are also difficultly soluble. The same can be said about the fatty acid with 10 carbon atoms even if the possibilities here are somewhat better. The acid with the odd number carbon atoms 9 is in pure condition difficult to have in solution under control in practice. Some tendencies of the same kind seem to characterize the acid with 7 carbon atoms!

However, the fatty acid with 8 carbon atoms — caprylic acid — is easy to dissolve in ammoniacal copper solution, and the acid with 6 carbon atoms — the caproic acid — enjoys good solution properties also. The caprylic acid has higher effect and gives more difficultly soluble and more difficultly voltile compounds in the wood or other fibrous material. These two acids have very good properties but the caprylic acid is to be preferred. The two acids are available in technical qualities.

The amount of fatty acids in the ammoniacal copper preservative can vary according to different demands from, for instance, half the copper content to an amount that corresponds to the stoichiometric ratio, that is up to about 4½ times the amount of copper. The lower amount of fatty acids is used when the effect of the preservative is based to a greater extent on the copper radical. This is when the demands on the resistance of the preservative against leaching, volatilizing and different kinds of conversion are specially high. The amount of fatty acid is increased in those cases where the preserving effect to a higher extent is based on the acid content of the composition.

The amount of fatty acids can be increased over the stoichiometric ratio. The surplus of fatty acids thus introduced will not and cannot be precipitated with copper: The surplus (over stoichiometric ratio) forms in the material — beside the copper compound of the fatty acid — also ammoniacal salts which gradually decompose to comparatively resistant free acids. Preservatives so composed are often used if only a limited preservation is needed. That is the preservation of fibrous material which is exposed to light leaching and evaporation only, or to a shorter protection against blue stain or mould eventually applied by dipping or a brush treatment. In some such cases the metal radical can be omitted, in consequence of which the whole preservative is then based solely on the fatty acid.

The following composition, in percent parts by weight, can be given as an example of a preservative for pressure treatment of wood:

| Copper | 10 per cent |
|---|---|
| Caprylic acid | 5 |
| Ammonia | 21 |
| Carbon dioxide | 37 |
| Water | 27 |

This preservative is as a rule manufactured as a moist blue powder. For the treatment of Swedish pine according to the Lowry method, this preservative is used in a 6 per cent water solution. For the Bethell method, half this strength i.e. 3 per cent, is used. As has been noted above, the amount of caprylic acid can be varied if desired. In the cases where a preservation against insects such as termites is wanted, arsenic — three or five valent — can be introduced in the preservative, for instance to an extent amounting to at least the half, and up to the whole, of the content of copper at the most. Such a preservative can for instance have the following composition (in weight percentages):

| Copper | 8 per cent |
|---|---|
| Caprylic acid | 4 |
| Arsenic, five valent | 4 |
| Ammonia | 21 |
| Carbon dioxide | 34 |
| Water | 29 |

The preserving agent remains in solution until the dissolving compounds — ammonia and carbon dioxide — have evaporated. The preservatives are also very suitable for use for more time-consuming treating processes. Earlier preservatives used for such purposes have either been fixed too early with poor distribution of the preservative in the wood as a consequence, or they have remained in solution and been satisfactorily distributed but the ensuing fixation has been very poor. Preservatives according to the invention remains in solution until the treatment is finished. They are enduringly fixed, but not before the so-treated wood is dried. The preservatives are thus quite suitable for these treatments including methods for replacing the sap with the treating solution as well as methods for diffusion treatments. The preservatives can be used for Boucheri treatments, for methods where moist wood is kept in strong preservative solutions from which the preservative enters into the wood by diffusion.

Spruce — normally very difficult to penetrate — can be treated with a good result by the Boucheri and diffusion methods. The spruce is penetrable in moist condition but not dried. A special spruce treatment is fulfilled in the following way.

The spruce is dried to some extent to leave a space for a solution later to be pressure-introduced. The drying may not be fulfilled too far as this will prevent the possibilities for penetration of the partly dried spruce. Then the spruce is Bethell-treated with a comparatively strong solution — for example, double normal strength. The solution penetrates into the outer parts of the wood until the wood has been saturated with the solution. After the treatment, the drying of the wood is prevented during some days or a couple of weeks depending on the dimensions and the temperature of the wood. During this period the preserving agent enters further into the wood by diffusion. Similar processes can be used for different, e.g., tropical woods, e.g., harder and some other kinds of wood difficult to penetrate. For these treatments it can be advantageous to increase the amount of dissolving ingredients. This is carried out simply by adding ammonia and carbon dioxide (ammonium bicarbonate) to the preservative. This can be done to a rather high excess, depending on the circumstances such as the dimensions of the wood, and the resistance the wood offers to the diffusion. Also, the temperature may influence the proportion. A high temperature facilitates the diffusion but it can also cause an increase in the evaporation of the solvents, ammonia and carbon dioxide. As a rule, the amount of ammonia and carbon dioxide for diffusion treatments may be increased by 50 to 100 per cent in comparison to the amount called for in pressure treatment.

A preservative for diffusion treatment can for instance, have the following composition in weight percentages:

| Copper | 6 per cent |
|---|---|
| Caprylic acid | 3 |

| -continued | |
|---|---|
| Ammonia | 20 |
| Carbon dioxide | 40 |
| Water | 31 |

For diffusion treatment this preservative may be used in 10 per cent (or stronger) solution.

By increasing the amount of ammonia and carbon dioxide in this way the precipitation of the preserving agents is delayed. The preserving agents get more time for diffusion. In special cases it can also be feasible to add limited amounts of substances which, with copper, form comparatively stable complexes that only slowly are converted. Such substances are for instance tartaric acid, malonic acid, and glycolic acid. In order to obtain more durable solutions and to diminish evaporation of ammonia and carbon dioxide, the solution can in use be covered with a thin layer of oil.

In the above discussion there has mainly been reference to wood preservation. As said in the general disclosure, the preservatives can be used for treatment of other organic fibrous materials. The methods of the treatment will in these cases be simpler because the preserving solution as a rule does not need to be introduced into the material by pressure. Very often a dipping, a brush treatment, etc., may be enough for the application. For such treatments very often a high amount of fatty acids in comparison to copper is to be preferred. The fatty acids may also be used solely dissolved in ammonia or alkali for instance for a surface protection of wood against blue stain, mould, and insects. If alkali is used for the dissolution of the acids they will remain leachable in the material to a much higher degree than if they are dissolved by ammonia.

The treatment method is a little different when wood pulp and other fiber suspensions are to be treated. If the purpose is to preserve paper exposed to severe attacks, the same preserving composition as used for wood can be used. If the question is to preserve wood pulp for a shorter period of storage, the amount of preservative can be considerably decreased and the content of the fatty acids in relation to copper can be relatively high. The fatty acids alone can even be used, dissolved by means of ammonia or alkali. The treatments can be carried out by adding the preservative, or a solution of it, to the pulp suspension in the pulp engine or "beater". When the preservative ingredients come into contact with the wood fibers a rather quick fixation of the preserving agents results.

Preservatives based on copper and fatty acids can also be used in oil solution. Some measures have to be taken before they can be dissolved in (for instance) petroleum products, especially if the copper content is high. The preservative has to be treated with a copper-dissolving oil such as naphthenic acid, or linolic acid and/or oleic acid (tall-oil). Thereafter, the copper-fatty-acids-products are dissolvable in different petroleum products and in organic solvents. When dissolving the preservative in this way in organic solvents, all active fatty acids can be included in the preservative without difficulty. Thus, it is easy to dissolve all fatty acids with between 6 and 12 carbon atoms (also others can be dissolved but they are of less interest). The amount of the dissolving oil may be rather low because the active fatty acid per se has some dissolving effect on the copper radical. This means that if more active fatty acid is used in the preservative less copper-dissolving oil is needed. If the copper content is high — especially if copper is present in stoichiometric surplus — more copper-dissolving oil is needed.

The following observations may be said about the normal fatty alcohols. They have high preserving properties similar to those of the fatty acids with an increasing effect with increased number of carbon atoms up to 10 carbon atoms; the 11 carbon alcohols has less effect and the 12 and higher carbon alcohols seem to have no effect. These alcohols cannot be dissolved in aqueous ammoniacal copper solution. They can, however, be introduced in the oily solution here described in the same way as the fatty acids.

Some examples of the preservatives dissolved in organic solvents may be given:

EXAMPLE 1

3.15 kilograms copper acetate, 4 kilograms caprylic acid, and 3 liters naphthenic acid were mixed and heated to 130° C. A solution was obtained which was diluted with petroleum product — boiling range 150°–225° C. — to 100 liters.

EXAMPLE 2

6.3 kilograms copper acetate, 4 kilograms caprylic acid, and 10 liters naphthenic acid were mixed and heated to 130° C. A solution was obtained which was diluted with petroleum product to 100 liters.

EXAMPLE 3

9.5 kilograms copper acetate, 4 kilograms caprylic acid, and 15 liters naphthenic acid were mixed and heated to 150° C. A solution was obtained which was diluted with petroleum product to 100 liters.

EXAMPLE 4

3.15 kilograms copper acetate, 4 kilograms caprylic acid, and 5 liters linolic acid were mixed and heated to 130° C. A solution was obtained which was diluted with petroleum product to 100 liters.

EXAMPLE 5

3.15 kilograms copper acetate, 4 kilograms caprylic acid, and 7 liters oleic acid were mixed and heated to 150° C. A solution was obtained which was diluted with petroleum products to 100 liters.

EXAMPLE 6

3.15 kilograms copper acetate, 4 kilograms mixed acids (40 per cent caprylic, 40 per cent caprin, and 20 per cent lauric acid) and 5 liters naphthenic acid were mixed and heated to 130° C. A solution was obtained which was diluted with petroleum product to 100 liters.

EXAMPLE 7

6.3 kilograms copper acetate, 4 kilograms mixed fatty acids, and 10 liters naphthenic acid were mixed and heated to 130° C. A solution was obtained which was diluted with petroleum product to 100 liters.

As noted above, the active fatty acids have a dissolving effect on the copper radical. This effect is, however, as a rule not sufficient for the dissolution even if the fatty acids are present in stoichiometric surplus. As an example of this it can be said that 3.15 kilograms copper acetate was mixed with 16 kilograms caprylic acid and heated to 150° C. The resulting product was diluted and dissolved in petroleum product. After an hour a precipitation was formed.

Instead of copper acetate other copper compounds can be used when making up the oil solutions; for example, copper carbonate and/or copper hydroxide. The dissolution proceeds in these cases more slowly. It is also possible to start with copper sulphate and react this with an alkali salt of the fatty acid, and then go further with the so-obtained copper-fatty-acid product.

To the preservatives dissolved in organic solvents there can be added different ingredients to give the preservative desired properties. Such ingredients can include: a drying oil such as linseed oil, or non-drying oil such as paraffine oil. In the first case a hard, and in second case, an oily water-repellent surface is obtained. Also different alcyde products, etc., can be introduced.

In order to increase the effect of the fatty acids they can to some degree be chlorinated or nitrated. This does not, however, necessarily give an advantage. The process causes some additional expense, and the obtained products are more harmful than are the fatty acid compositions.

In the above the discussion has related to copper as active positive agent. Other metals can be used, but as a rule they do not have the same good properties. These metals are for example zinc, cadmium, nickel and/or cobalt.

I claim:

1. Preservative for wood and other organic fiber products consisting essentially of a copper compound and a fatty acid having from 6 to 12 carbon atoms per molecule dissolved in an aqueous ammoniacal solution.

2. Preservative according to claim 1 which additionally contains carbon dioxide in solution and, wherein the amount by weight of ammonia is about double the amount of copper, and the amount of carbon dioxide is about double the amount of the ammonia.

3. Preservative according to claim 1, wherein the solution has the following composition in weight percentages:

| | | |
|---|---|---|
| copper | | 0.6 per cent |
| caprylic acid | | 0.3 – 0.6 |
| ammonia | | 1.2 |
| carbon dioxide | | 2.2 |
| water | up to | 100.0 |

4. Preservative according to claim 1, wherein the solution has the following composition in weight percentages:

| | | |
|---|---|---|
| copper | | 0.6 per cent |
| caprylic acid | | 0.3 |
| arsenic, five valent | | 0.3 |
| ammonia | | 1.5 |
| carbon dioxide | | 2.5 |
| water | up to | 100.0 |

5. Preservative according to claim 1, wherein the solution has the following composition in weight percentages:

| | | |
|---|---|---|
| copper | | 0.6 per cent |
| caprylic acid | | 0.3 – 0.6 |
| ammonia | | 2.0 |
| carbon dioxide | | 4.0 |
| water | up to | 100.0 |

6. Wood preservative mixture having the following composition in weight percentages:

| | |
|---|---|
| copper | 10 per cent |
| caprylic acid | 5 |
| ammonia | 21 |
| carbon dioxide | 37 |
| water | 27 |

7. Wood preservative mixture having the following composition in weight percentages:

| | |
|---|---|
| copper | 6 per cent |
| caprylic acid | 3 |
| ammonia | 20 |
| carbon dioxide | 40 |
| water | 31 |

8. Preservative for wood and other organic fiber products consisting essentially of a copper compound and a fatty acid selected from the group consisting of caproic, caprylic and capric acid, dissolved in an aqueous ammoniacal solution.

9. Preservative according to claim 8, wherein said fatty acid is caprylic acid.

10. Preservative according to claim 8, wherein said copper compound is dissolved in an aqueous solution of ammonium bicarbonate.

* * * * *